United States Patent [19]

Gluchowski et al.

[11] Patent Number: 5,418,234
[45] Date of Patent: May 23, 1995

[54] METHODS FOR USING (2-IMIDAZOLIN-2-YLAMINO) QUINOXALINE DERIVATIVES

[75] Inventors: Charles Gluchowski, Pompton Lakes, N.J.; Michael E. Garst, Newport Beach, Calif.; James A. Burke, Tustin, Calif.; Larry A. Wheeler, Irvine, Calif.; Michael E. Garst, Newport Beach, Calif.

[73] Assignee: Allergan, Inc., Irvine, Calif.

[21] Appl. No.: 298,494

[22] Filed: Aug. 30, 1994

Related U.S. Application Data

[60] Division of Ser. No. 195,184, Feb. 10, 1994, Pat. No. 5,373,010, which is a division of Ser. No. 10,954, Jan. 29, 1993, Pat. No. 5,326,763, which is a division of Ser. No. 820,329, Jan. 13, 1992, Pat. No. 5,231,096, which is a continuation-in-part of Ser. No. 758,696, Sep. 12, 1991, Pat. No. 5,204,347, which is a division of Ser. No. 420,817, Oct. 12, 1989, Pat. No. 5,077,292, and a continuation-in-part of Ser. No. 560,776, Jul. 31, 1990, Pat. No. 5,112,822, which is a continuation-in-part of Ser. No. 420,817, Jul. 31, 1990.

[51] Int. Cl.⁶ ................ A61K 31/495; A61K 31/50
[52] U.S. Cl. ........................... 514/249; 514/816
[58] Field of Search .................... 514/249, 816

[56] References Cited

U.S. PATENT DOCUMENTS

| | | | |
|---|---|---|---|
| 3,890,319 | 6/1975 | Danielewicz et al. | 544/353 |
| 5,077,292 | 12/1991 | Gluchowski | 514/249 |
| 5,112,822 | 5/1992 | Gluchowski | 514/249 |
| 5,198,442 | 3/1993 | Gluchowski | 514/249 |
| 5,231,096 | 7/1993 | Gluchowski | 514/249 |
| 5,326,763 | 7/1994 | Gluchowski | 514/249 |

FOREIGN PATENT DOCUMENTS

| | | |
|---|---|---|
| 0422878 | 4/1991 | European Pat. Off. . |
| 0426390 | 5/1991 | European Pat. Off. . |
| 2538620 | 3/1976 | Germany . |
| WO8911851 | 12/1989 | WIPO . |
| 9202515 | 2/1992 | WIPO . |

OTHER PUBLICATIONS

Fielding, "Clonidine; New Research in Psychotropic Drug Pharmacology", Medicinal Research Reviews, vol. 1, No. 1 pp. 97–123 (1981).

Isom et al, "a2–Adrenergic Receptors Accelerate Na/H Exchange in Neuroblastoma X Glioma Cells," The (List continued on next page.)

*Primary Examiner*—Raymond Henley, III
*Assistant Examiner*—Kimberly R. Jordan
*Attorney, Agent, or Firm*—Frank J. Uxa

[57] ABSTRACT

A method of treating a mammal comprises administering to a mammal an effective amount to provide a desired therapeutic effect in the mammal of a compound selected from the group consisting of those having the formula:

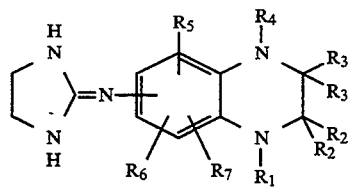

, pharmaceutically acceptable acid addition salts thereof and mixtures thereof, wherein $R_1$ and $R_4$ are independently selected from the group consisting of H and alkyl radicals having 1 to 4 carbon atoms; the $R_2$s are independently selected from H or alkyl radicals having 1 to 4 carbon atoms or are, together, oxo; the $R_3$s are independently selected from H or alkyl radicals having 1 to 4 carbon atoms or are, together, oxo; the 2-imidazolin-2-ylamino group may be in any of the 5-, 6-, 7- or 8-positions of the quinoxaline nucleus; and $R_5$, $R_6$ and $R_7$ each is located in one of the remaining 5-, 6-, 7- or 8-positions of the quinoxaline nucleus and is independently selected from the group consisting of Cl, Br, H and alkyl radicals having 1 to 3 carbon atoms. Such compounds, when administered to a mammal, provide desired therapeutic effects, such as reduction in peripheral pain and reduction in or prevention of at least one effect of ischemia.

19 Claims, No Drawings

OTHER PUBLICATIONS

Journal of Biological Chemistry vol. 262, No. 14, Issue of May 15, 1987, pp. 6750–6757.

Pieter, et al, "Clonidine and Some Bridge Analogues; Cardiovascular Effects and Nuclear Magnetic Resonance Data ($^1H/^{13}$)," Eur. J. Med. Chem, Jul.–Aug. 1980, vol. 4, pp. 323–329.

Gellai et al, "Renal Effects of Selective Alpha-1 and Alpha-2 Adrenoceptor Agonists in Conscious, Normotensive Rats", The Journal of Pharmacology, vol. 240, 1986.

Jarrot, "Clonidine and Related Compounds", Handbook of Hypertension, vol. 5 (1984).

Bloor et al, "Reduction in Halothane Anesthetic Requirement by Clonidine, an Alpha–Adrenergic Agonist", Anesthesia & Analgesia, vol. 61, No. 9, Sep. 1982 (741–745).

Zwieten et al, "Central & Perpiphera a-Adrenoceptors. Pharmacological Aspects & Clinical Potential," Advances in Drug Research vol. 13, 1984 (209–254).

Gellai et al, "Mechanism of a2-adrenoceptor agonist–induced diuresis" American Physiological Society 1988.

a2-Adrenergic Agonists: A Newer Class of Antidiarrheal Drug Gastroenterology 1986, vol. 91 pp. 769–775.

Mittag, "Ocular Effects of Selective Alpha–Adrenergic Agents: A New Drug Paradox?", Annals of Ophthalmology Mar. 1983.

Jumblatt et al, "Alpha-2 Adrenergic Modulation of Norepinephrine Secretion in the Perfused Rabbit Iris–Ciliary Body," Current Eye Research, 1987, vol. 6, pp. 767–777.

Burke et al, "Ocular Effects of a Relatively Selective a2 Agonist (UK–14, 304–18) in cats, rabbits and monkeys," Current Eye Research, 1986, vol. 5, pp. 665–676.

Fondacaro et al, "Selective Alpha-2 Adrenoceptor Agonists Alter Fluid and Electrolyte Transport in Mammalian Small Intestine" American Society for Pharmacology, vol. 247, 1987.

Langer et al, "Pharmacologic and Therapeutic Significance of a-Adrenoceptor Subtypes", Journal of Cardiovascular Pharmacology, vol. 7, Supp. 8 (S1–S8) (1985).

Nielsen et al, "Postjunctional $a_2$]adrenoceptors mediate vasoconstrict in human subcutaneous resistance vessels", Br. J. Pharmacol (1989), 97 (829–834).

B. Bloor, "Clonidine and Other Alpha$_2$Adrenergic Agonists: An Important New Drug Class for the Perioperative Period", Seminars in Anesthesia, vol. VII, No. 3 (Sep.), 1988: (pp. 170–177).

Sato et al, "Adrenergic Excitation of Cutaneous Pain Receptors Induced by Peripheral Nerve Injury", Science, vol. 251, (Mar.), 1991), (pp. 1608–1610).

Bendele, et al, "Anti–Inflammatory Activity of Pergolide in Rats", Pharmacol (Aug.) 1991, (p. 152), 82.

Hieble, et al, "A Potent Peripherally Acting, $A_2$Adrenoceptor Agonist" The Pharmologist (1991), vol. 33, #3 (p. 214).

*The Pharmacological Basis of Therapeutics,* Gilman & Goodmen, 1985, "Therapeutic Uses of Sympathomimetic Drugs", (pp. 174–179), 7th Edition, Chapter 8.

Ekas et al, Increased presynaptic alpha–adrenoceptor mediated regulation of spontaneously hypertensive rats, Chemical Abstracts, vol. 98, No. 1, Jan. 3, 1983, p. 918.

De Mey et al, Differences in pharmacological properties of postjunctional alpha–adrenergic receptors among arteries and veins, Chemical Abstracts, vol. 93, No. 13, Sep. 29, 1980, p. 96.

Walland, Inhibition of a somato-sympathetic reflex via peripheral presynaptic alpha–adrenoceptors, Chemical Abstracts, vol. 88, No. 23, Jun. 5, 1978, p. 80.

C. F. Colpaert, Maximal magnitude of effect and potency of putative alpha–adrenoceptor agonists in causing CNS depression, in relaxing muscle, and in lowering body temperature in rat, Chemical Abstracts, vol. 105, No. 1, Jul. 7, 1986, p. 45.

Philippu et al, Changes in the arterial blood pressure increase the release of endogenous histamine in the hypothalamus of anesthetized cats, Chemical Abstracts, vol. 99, No. 15, Oct. 10, 1983, p. 137.

Ekas et al, Presynaptic alpha– and beta–adrenoceptor stimulation and norepinephrine release in the spontaneously hypertensive rat, Chemical Abstracts, vol. 98, No. 45, p. 109 (1983).

Steppler et al, Pre– and postsynaptic effects of phenylephrine and tramazoline on blood vessels in vivo, Chem. Abstracts, vol. 91, No. 21, Nov. 19, 1979, p. 43.

Steppeler et al, A comparison of pre– and postsynaptic alpha–adrenergic effects of phenylephrine and tramazoline on blood vessels of the rabbit in vivo, Chem. Abstracts, vol. 90, No. 5, Jan. 29, 1979, p. 37.

Timmermans et al, Hypotensive and bradycardic effects of classical alpha–sympathomimetic drugs upon intravenous administration to pentobarbiton–anesthetized rate, Chem. Abstract, vol. 89, No. 1, Jul. 3, 1978, p. 49.

Boudier et al, Central and peripheral alpha adrenergic acitivty of imidazoline derivatives, Chemical Abstract, vol. 82, No. 17, Apr. 28, 1975, p. 13.

METHODS FOR USING (2-IMIDAZOLIN-2-YLAMINO) QUINOXALINE DERIVATIVES

RELATED APPLICATION

This application is a division of application Ser. No. 08/195,184, filed Feb. 10, 1994, which, in turn is a division of application Ser. No. 08/010,954, filed Jan. 29, 1993, now U.S. Pat. No. 5,326,763, which, in turn, is a division of application Ser. No. 07/820,329, filed Jan. 13, 1992, now U.S. Pat. No. 5,231,096, which, in turn, is a continuation-in-part of application Ser. No. 07/758,696 filed Sep. 12, 1991, now U.S. Pat. No. 5,204,347, which, in turn, is a division of application Ser. No. 07/420,817 filed Oct. 12, 1989, now U.S. Pat. No. 5,077,292; and a continuation-in-part of application Ser. No. 07/560,776 filed Jul. 31, 1990, now U.S. Pat. No. 5,112,822 which, in turn, is a continuation-in-part of application Ser. No. 07/420,817, filed Oct. 12, 1989, now U.S. Pat. No. 5,077,292.

BACKGROUND OF THE INVENTION

The present invention relates to novel substituted derivatives of quinoxaline. More particularly, the invention relates to such derivatives which are useful as therapeutic agents, for example, to effect reduction in intraocular pressure, to increase renal fluid flow and to effect an alteration in the rate of fluid transport in the gastrointestinal tract.

Various quinoxaline derivatives have been suggested as therapeutic agents. For example, Danielewicz, et al U.S. Pat. No. 3,890,319 discloses compounds as regulators of the cardiovascular system which have the following formula:

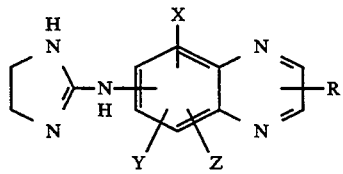

where the 2-imidazolin-2-ylamino group may be in any of the 5-, 6-, 7- or 8-position of the quinoxaline nucleus; X, Y and Z may be in any of the remaining 5-, 6-, 7- or 8-positions and may be selected from hydrogen, halogen, lower alkyl, lower alkoxy or trifluoromethyl; and R is an optional substituent in either the 2- or 3-position of the quinoxaline nucleus and may be hydrogen, lower alkyl or lower alkoxy.

SUMMARY OF THE INVENTION

New methods for treating mammals, preferably human beings, to provide a desired therapeutic effect have been discovered. By administering an effective amount of one or more of certain compounds to a mammal, a desired therapeutic effect is provided in the mammal. Such desired therapeutic effects include reduction in peripheral pain, anesthetization of the central nervous system, constriction of one or more blood vessels, reduction in or prevention of at least one effect of ischemia, decongestion of one or more nasal passages, and reduction in at least one effect of an inflammatory disorder.

The compounds which are administered in the methods of the present invention are those having the formula:

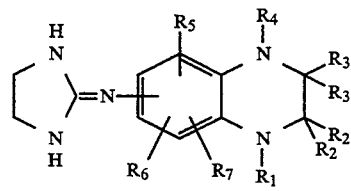

and pharmaceutically acceptable acid addition salts thereof and mixtures thereof, wherein $R_1$ and $R_4$ are independently selected from the group consisting of H and alkyl radicals having 1 to 4 carbon atoms; the $R_2$s are independently selected from H or alkyl radicals having 1 to 4 carbon atoms or are, together, oxo; the $R_3$s are independently selected from H or alkyl radicals having 1 to 4 carbon atoms or are, together, oxo; the 2-imidazolin-2-ylamino group may be in any of the 5-, 6-, 7- or 8-positions of the quinoxaline nucleus; and $R_5$, $R_6$ and $R_7$ each is located in one of the remaining 5-, 6-, 7- or 8-positions of the quinoxaline nucleus and is independently selected from the group consisting of Cl, Br, H and alkyl radicals having 1 to 3 carbon atoms.

Particularly useful compounds are those in which $R_1$ and $R_4$ are H, the 2-imidazolin-2-ylamino group is in the 6-position of the quinoxaline nucleus, $R_5$ is selected from the group consisting of Cl, Br and alkyl radicals containing 1 to 3 carbon atoms, more preferably Br, and is in the 5-position of the quinoxaline nucleus, and $R_6$ and $R_7$ are H. Each of the $R_2$s and each of the $R_3$s is preferably independently selected from H and alkyl radicals having 1 to 4 carbon atoms, more preferably from H and methyl radical.

In one embodiment, at least one of the $R_2$s and at least one of the $R_3$s are H. At least one of the $R_2$s or at least one of the $R_3$s may be methyl radical. The $R_2$s and the $R_3$s that are not alkyl, e.g., methyl, radicals, are H, or together is oxo. At least one of the $R_2$s may be different from at least one of the $R_3$s.

Pharmaceutically acceptable acid addition salts of the compounds of the invention are those formed from acids which form non-toxic addition salts containing pharmaceutically acceptable anions, such as the hydrochloride, hydrobromide, hydroiodide, sulphate or bisulfate, phosphate or acid phosphate, acetate, maleate, fumarate, oxalate, lactate, tartrate, citrate, gluconate, saccharate and p-toluene sulphonate salts.

DETAILED DESCRIPTION OF THE INVENTION

The present invention involves methods for treating mammals to provide one or more desired therapeutic effects in the mammal. The present methods comprise administering an effective amount to provide the desired therapeutic effect or effects in a mammal of at least one compound, as described herein, to the mammal. Among the desired therapeutic effects are reduction in peripheral pain, anesthetization of the central nervous system, constriction of one or more blood vessels, reduction in or prevention of at least one effect of ischemia, decongestion of one or more nasal passages and reduction in at least one effect of an inflammatory disorder, for example, such disorders characterized by progressive joint and/or tissue deterioration. Thus, for example, the presently useful compounds may be effective as one or more of the following: a peripheral pain killing agent, a general anesthetic, a vaso-constricting agent, an agent for the treatment of ischemia, a nasal decongestant, and an anti-inflammatory agent. One important feature of many of the present methods is that the desired therapeutic effect is achieved with reduced side effects, in particular with reduced effects on the blood pressure of the mammal to which the presently useful compound or compounds are administered.

Any suitable method of administering the presently useful compound or compounds to the mammal to be treated may be used. The particular method of administration chosen is preferably one which allows the presently useful compound or compounds to have the desired therapeutic effect in an effective manner, e.g., low medication concentration and low incidence of side effects. In many applications, the presently useful compound or compounds are administered to a mammal in a manner substantially similar to that used to administer alpha agonists, in particular alpha 2 agonists, to obtain the same or similar therapeutic effect or effects.

Administration of the presently useful compounds for use in the methods of this invention can include, but are not limited to, oral, parenteral, topical, intra-articular and other modes of systemic administration. The compounds are administered in a therapeutically effective amount either alone or in combination with a suitable pharmaceutically acceptable carrier or excipient.

Depending on the intended mode of administration, the presently useful compound or compounds may be incorporated in any pharmaceutically acceptable dosage form, thereof such as for example, tablets, suppositories, pills, capsules, powders, liquids, suspensions, emulsions, aerosols or the like, preferably in unit dosage forms suitable for single administration of precise dosages, or sustained release dosage forms for continuous controlled administration. Preferably the dosage form will include a pharmaceutically acceptable excipient and the presently useful compound or compounds and, in addition, may contain other medicinal agents, pharmaceutical agents, carriers, adjutants, etc.

For solid dosage forms, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. An example of a solid dosage form for carrying out the invention is a suppository containing propylene glycol as the carrier. Liquid pharmaceutically administrable dosage forms can, for example, comprise a solution or suspension of one or more of the presently useful compounds and optional pharmaceutical adjutants in a carrier, there such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgement of the prescribing physician. The therapeutically effective dosage of the presently useful compound or compounds is preferably in the range of about 0.5 or about 1 to about 100 mg/kg/day.

The presently useful compounds are as described above. All stereoisomers, tautomers and mixtures thereof which comply with the constraints of one or more formulae of the presently useful compounds are included within the scope of the present invention. For example, both tautomers

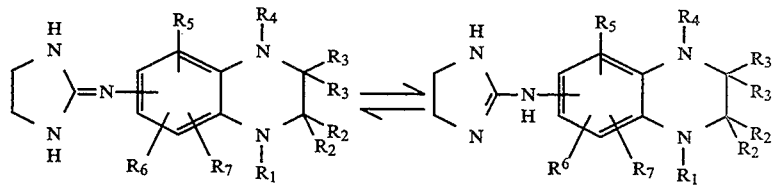

are within the scope of the present invention.

The presently useful compounds may be prepared in a manner analogous to the procedures described in Danielewicz, et al U.S. Pat. No. 3,890,319 for the production of the quinoxaline derivatives therein. This patent is hereby incorporated in its entirety by reference herein. Once a 2-imidazolin-2-ylamino quinoxaline intermediate corresponding to the compound described in Danielewicz, et al U.S. Pat. No. 3,890,319 is obtained, this 2-imidazolin-2-ylamino quinoxaline intermediate is hydrogenated to saturate any unsaturation at the 1-, 2-, 3-, and 4-positions of the quinoxaline nucleus.

Briefly, the 2-imidazolin-2-ylamino quinoxaline intermediates may be prepared by (1) reaction of the appropriate amino-quinoxaline with thiophosgene to form the corresponding isothiocyanate; and (2) reacting this isothiocyanate with excess ethylenediamine to form the corresponding beta-aminoethyl-thioureidoquinoxaline, which is then cyclized to the corresponding intermediate. Alternately, such intermediates can be prepared by (1) reacting the corresponding aminoquinoxaline with benzoyl isothiocyanate to form the corresponding N-benzoyl thioureido compound, followed by hydrolysis to the thioureido compound, or reaction of the aminoquinoxaline with ammonium thiocyanate to form the thioureido compound directly; (2) methylation to form the S-methyl deviation of the thioureido compound; and (3) reaction with ethylene diamine to form the intermediate.

The 2-imidazolin-2-ylamino quinoxaline intermediate is then reacted to saturate any unsaturation at the 1-, 2-, 3-, and 4-positions of the quinoxaline nucleus. For compounds in which $R_1$, the $R_2$'s, the $R_3$'s and $R_4$ are all to be H, the intermediate may be hydrogenated. This hydrogenation preferably occurs with the intermediate dissolved in a liquid, e.g., a lower alcohol such as methanol, ethanol or the like. A catalyst effective to promote the hydrogenation is preferably present. Examples of such catalysts include the platinum group metals, in particular platinum, platinum group metal compounds, such as platinum oxide, and mixtures thereof. Hydrogen, e.g., free molecular, hydrogen, is present in an amount at least sufficient to provide the desired saturation, preferably in an amount in excess of that required to provide the desired saturation, of the intermediate. The temperature and pressure at which the hydrogenation occurs are preferably selected to maintain the intermediate and final product substantially in the liquid phase. Temperatures in the range of about 10° C. to about 100° C. and pressures in the range of about 0.5 atmospheres to about 5 atmospheres often provide acceptable results. These conditions are maintained for a time sufficient to provide the desired hydrogenation reaction. This period of time is often in the range of about 1 minute to about 2 hours. The final 2-imidazolin-2-ylamino tetrahydroquinoxaline is separated from the hydrogenation reaction mixture and recovered, e.g., using conventional techniques.

For compounds in which $R_1$, the $R_2$'s, the $R_3$'s and $R_4$ are all to be H and for compounds in which $R_1$ and $R_4$ are to be H and at least one of the $R_2$s and/or at least one of the $R_3$s are to be alkyl, the intermediate may be reacted with a suitable hydride reducing agent. This reaction preferably occurs with the intermediate and the hydride reducing agent dissolved in a liquid. Any suitable hydride reducing agent may be employed. Examples of useful hydride reducing agents include NaBH4, NaCNBH4, LiAlH4 and the like. The amount of hydride reducing agent used should be sufficient to saturate all the unsaturation present at the 1-, 2-, 3- and 4-positions of the intermediate. Excess hydride reducing agent may be employed provided that no deterioration of the final tetrahydroquinoxaline product results. The liquid employed should be such as to act as an effective solvent for the intermediate and the hydride reducing agent, and may also function to facilitate, e.g., activate, the reaction between the intermediate and hydride reducing agent. Examples of useful liquids include acetic acid, trifluoroacetic acid, tetrahydrofuran, diethyl ether and the like. The liquid employed is preferably selected so as to avoid excess hydride reducing agent reactivity. For example, where LiAlH4 is used as the hydride reducing agent, the liquid is preferably tetrahydrofuran, diethyl ether and the like. One or more co-solvents, e.g., lower alcohols, may also be used. The temperature and pressures at which the reaction occurs are preferably selected to maintain the intermediate and final product in the liquid phase. Temperatures in the range of about 0° C. to about 50° C. and pressures in the range of about 0.5 atmospheres to about 2 atmospheres often provide acceptable results. Reaction time is chosen to allow the desired reaction to occur, and is often in the range of about one minute to about one hour. The final 2-imidazolin-2-ylamino tetraquinoxaline is separated from the reactive mixture and recovered, e.g., using conventional techniques, such as evaporation, deactivation of the excess hydride reducing agent, extraction and chromatographic separation.

For compounds in which $R_1$ and/or $R_4$ are to be alkyl, the intermediate (having no substituents corresponding to $R_1$ and $R_4$) may be reacted with a suitable hydride reducing agent in the presence of a selected aldehyde or aldehydes. The aldehyde or aldehydes used are selected based on the specific $R_1$ and/or $R_4$ alkyl group or groups desired. For example, if $R_1$ and/or $R_4$ is to be methyl, formaldehyde is used, if $R_1$ and/or $R_4$ is to be ethyl, acetaldehyde is used, etc. The reaction conditions used are similar to those described in the immediately preceding paragraph except that the reaction time is often in the range of about 1 hour to about 24 hours. The amount of aldehyde used may vary depending on the final compound desired. A mixture of final compounds, i.e., a compound in which both $R_1$ and $R_4$ are alkyl mixed with compounds in which only one of $R_1$ or $R_4$ is alkyl, may be produced by the reaction. One or more individual tetrahydroquinoxalines useful in the present invention can be separated and recovered from this mixture, e.g., using conventional techniques.

The presently useful compounds may be prepared from available starting materials. For example, 4-nitro-1,2-phenylenediamine may be reacted with an appropriate halide substituted carbonyl halide, in particular, a bromide substituted carbonyl bromide. This reaction, which provides for substitution of one of the amine groups on the phenylene ring by the carbonyl halide, is preferably conducted in a solvent and preferably at a temperature in the range of about 10° C. to about 50° C., in particular about room temperature. Reaction pressure is preferably such that the solvent is maintained substantially in the liquid phase. The reaction preferably occurs over a period of time in the range of about 2 hours to about 24 hours. Examples of useful solvents include methylene chloride ($CH_2Cl_2$), chloroform ($CHCl_3$), tetrahydrofuran and the like. A trialkyl amine, e.g., triethylamine, may be used as part of the solvent and/or to promote or facilitate the substitution reaction.

The resulting mixture of halo amide isomers are recovered preferably by conventional techniques, e.g., extraction, washing, drying, concentration, chromatography and the like, from the substitution reaction mixture. The isomers are then cyclized. This cyclization is preferably effected at a temperature in the range of about 10° C. to about 50° C., in particular at room temperature, by contacting the isomers, preferably dissolved in a solvent such as methylene chloride, with a cyclizing agent, such as $AgBF_4$, $AgNO_3$ and the like. Reaction pressure is preferably such that the solvent is maintained substantially in the liquid phase. The reaction preferably occurs over a period of time in the range of about 1 hour to about 24 hours. Conventional techniques, e.g., such as noted above, can be used to recover the cyclized isomers. Chromography can be used to separate the isomers and provide them in substantially pure form.

The cyclized compound produced as described above, identified as a nitro-substituted quinoxalinone, is hydrogenated to convert the nitro group to an amino group. This hydrogenation preferably occurs with the nitro-substituted quinoxalinone dissolved in a liquid, e.g., a lower alcohol such as methanol, ethanol or the like. A catalyst effective to promote the hydrogenation is preferably present. Examples of such catalysts include the platinum group metals, in particular platinum or palladium, platinum group metal compounds, such as platinum oxide or palladium oxide, and mixtures thereof. Hydrogen, e.g., free molecular hydrogen, is present in an amount at least sufficient to provide the desired hydrogenation, preferably in an amount in excess of that required to provide the desired hydrogenation. The temperature and pressure at which the hydrogenation occurs are preferably selected to maintain the nitro-substituted quinoxalinone and hydrogenated product substantially in the liquid phase. Temperatures in the range of about 10° C. to about 100° C. and pressures in the range of about 0.15 atmospheres to about 5 atmospheres often provide acceptable results. These conditions are maintained for a time sufficient to provide the desired hydrogenation reaction. This period of time is often in the range of about 1 hour to about 16 hours. The hydrogenated product is separated from the hydrogenation reaction mixture and recovered, e.g., using conventional techniques.

At this point, the hydrogenated product may be subjected to one or more reactions to include one or more groups in the compound, as desired. For example, in one embodiment, it is preferred that the final quinoxaline derivative of the present invention includes at least one halide group, in particular a bromo group, on the aromatic ring structure. In order to provide such a bromo group, the above-noted hydrogenated product is brominated. Such bromination can occur by dissolving the hydrogenated product in a suitable solvent, e.g., glacial acetic acid, trifluoroacetic acid and the like, and contacting this solution with bromine. The mixture is preferably maintained at a suitably low temperature, e.g., in the range of about 10° C. to about 50° C., so that the degree of bromination can be controlled. Cooling or removing heat from the reaction mixture may be desirable. Room temperature bromination provides satisfactory results. Reaction pressure is preferably such that the solvent is maintained substantially in the liquid phase. The reaction preferably occurs over a period of time in the range of about 0.25 hours to about 6 hours. Conventional techniques, e.g., vacuum filtration, can be used to recover the brominated product, which may be a hydrobromide salt.

The above-noted hydrogenated product or substituted hydrogenated product is reacted with 2-imidazoline-2-sulfonic acid to produce a 2-imidazolin-2-ylamino quinoxaline derivative useful in the present invention. Such derivatives include an oxo group. This reaction can occur by dissolving the reactants in an appropriate solvent, e.g., an alcohol such as isobutanol, and heating this solution to reflux at atmospheric pressure. Preferred reaction temperatures are in the range of about 70° C. to about 150° C. Reaction pressure is preferably such that the solvent is refluxed or maintained substantially in the liquid phase. The reaction preferably occurs over a period of time in the range of about 1 hour to about 24 hours. Conventional techniques, e.g., concentration and chromatography, can be used to recover the desired quinoxaline derivative.

The present quinoxaline derivatives which do not include an oxo group can be obtained by reacting the above-described oxo-containingquinoxaline derivatives to remove the oxo group. This can be accomplished by dissolving the oxo-containing material in an appropriate solvent, e.g., tetrahydrofuran, acetic acid, trifluoroacetic acid, diethyl ether and the like, and subjecting this solution to a hydride reducing agent, such as LiAlH$_4$, NaBH$_4$, NaCNBH$_3$ and the like. Reaction temperatures in the range of about 20° C. to about 100° C. can be used. Conventional techniques, e.g., cooling, concentration and chromatography, can be employed to provide the present quinoxaline derivative which do not include an oxo group.

Specific examples of compounds which are useful in the present invention include those which have the following formulas:

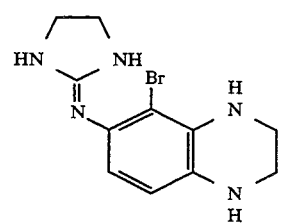

I

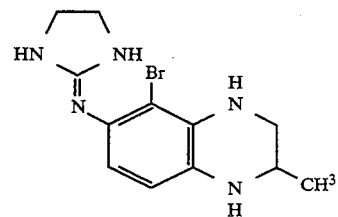

II

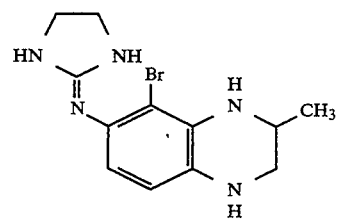

III

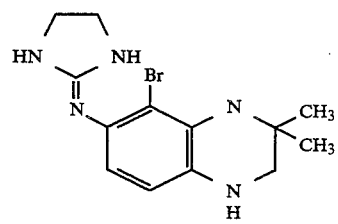

IV

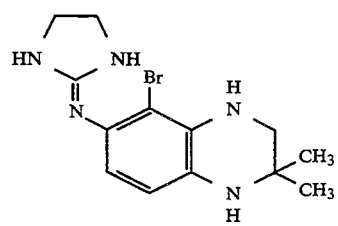

V

-continued

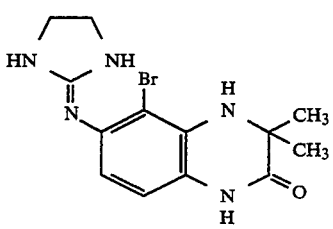

VI

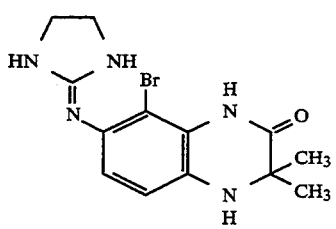

VII

, pharmaceutically acceptable acid addition salts thereof and mixtures thereof. Compounds having formula (I), pharmaceutically acceptable acid addition salts thereof and mixtures thereof are particularly useful.

The present compound or compounds may be included in a medication composition together with one or more other components to provide a medication composition which can be effectively administered. Such other components, e.g., carriers, anti-oxidants, bulking agents and the like, may be chosen from those materials which are conventional and well known in the art, e.g., as being included in medication compositions with alpha 2 agonists.

The following non-limiting examples illustrate certain aspects of the present invention.

EXAMPLE 1

Preparation of
5-Bromo-6-(2-imidazolin-2-ylamino)-1,2,3,4-tetrahydroquinoxaline 1,2,4-Triaminobenzene dihydrochloride To a suspension of 4-nitrophenylenediamine (Aldrich, 10 g, 65.3 mmol) in absolute ethanol (240 ml) was added 600 mg of 10% by weight palladium on charcoal catalyst. The container including the suspension was evacuated and filled with hydrogen three times and the suspension was hydrogenated at 18 psi until hydrogen uptake ceased. The reaction was slightly exothermic and one refill of hydrogen was required. The resulting light yellow solution, which darkens rapidly on contact with air, was filtered and concentrated to about 150 ml. Concentrated hydrochloric acid (12 ml) was added and the solid formed was filtered off. After drying in vacuo overnight, 12 g (a yield of 93%) of purple solid was obtained, m.p. 224°–5° C. Using various analytical procedures, this solid was determined to be 1,2,4-triaminobenzene dihydrochloride.

6-Aminoquinoxaline

Glyoxal sodium bisulfite adduct (Aldrich, 14.3 g, 50 mmol) was added in small portions to a solution of 1,2,4-triaminobenzene dihydrochloride (9.8 g, 50 mmol) in 200 ml of 10% by weight sodium carbonate in water. The reaction mixture was heated to 100° C. for two hours and then cooled to 0° C. The crystals formed were filtered off and dried in vacuo to give a crude yield of 7.06 g (a yield of 97%) of brown crystals. Recrystallization from benzene gave 6.32 g (a yield of 87%) yellow crystals, m.p. 157°–8° C. Using various analytical procedures, these yellow crystals were determined to be 6-aminoquinoxaline.

6-Amino-5-bromoquinoxaline hydrobromide

6-Aminoquinoxaline (2.08 g, 14.4 mmol) was dissolved in 11.5 ml glacial acetic acid. The solution was cooled in water while a solution of bromine (0.74 ml, 2.3 g, 14.4 mmol) in 1.5 ml glacial acetic acid was added slowly over 15 min. After stirring for an additional 30 min, the orange red solid formed was filtered off and washed thoroughly with dry ether. The solid was dried in vacuo overnight to yield 4.44 g crude product (a yield of 100%). The compound, 6-amino-5-bromoquinoxaline hydrobromide, had no definite melting point. A phase change (from fine powder to red crystals) was noticed at about 220° C. Decomposition was observed at about 245° C. It was used directly for the next step.

6-Amino-5-Bromoquinoxaline

The crude 6-amino-5-bromoquinoxaline from above was dissolved in water and saturated sodium bisulfite solution was added until the resulting solution tested negative with starch-iodide paper. The solution was then basified with 2N sodium hydroxide and extracted thoroughly with ethyl acetate. The organic extract was dried over magnesium sulfate and concentrated under reduced pressure to give the free base. The crude product was recrystallized from boiling benzene to give yellow crystals, m.p. 155°–6° C. Using various analytical procedures, the yellow crystals were determined to be 6-amino-5-bromoquinoxaline. The yield was 82%.

5-Bromo-6-isothiocyanatoquinoxaline

The crude hydrobromide product previously noted (4.27 g, 14.0 mmol) was dissolved in 60 ml of water and thiophosgene (Aldrich, 1.28 ml, 16.8 mmol) was added in small portions with vigorous stirring. After 2 hours, the red color of the solution was discharged. The solid formed was filtered off and washed thoroughly with water. After drying in vacuo at 25° C., 3.38 g (a yield of 90%) of brick red crystals was obtained, m.p. 157°–8° C. A portion of this material was further purified by column chromatography to give white crystals, m.p. 157°–8° C. Using various analytical procedures, these crystals were determined to be 5-bromo-6-isothiocyanatoquinoxaline.

5-Bromo-6(-N-(2-aminoethyl)thioureido)quinoxaline

A solution of the isothiocyanate (3.25 g, 12.2 mmol) in 145 ml benzene was added to a solution of ethylenediamine (Aldrich, 5.43 g, 90.0 mmol) in 18 ml benzene at 25° C. over 2 hours. After stirring for a further 30 min., the supernatant was poured off. The oil which remained was washed by swirling with dry ether three times and used directly for the next step.

A portion of this product was further purified by column chromatography (SiO₂, CHCl₃) for characterization. A white solid was recovered which decomposed at 175° C. with gas evolution (puffing). This white solid was determined to be 5-bromo-6(-N-2-(aminoethyl)thioureido)quinoxaline.

5-Bromo-6-(2-imidazolin-2-ylamino)quinoxaline

The crude product from above was dissolved in 100 ml dry methanol and the brown solution was refluxed for 19 hours until hydrogen sulfide gas was no longer evolved. The mixture was cooled to room temperature and concentrated to about 50 ml. The yellow solid was filtered off and dried in vacuo; weight 2.52 g (a yield of 70%), mp 242°14 4° C.

As the crude product was insoluble in most common organic solvents, initial purification was achieved by an acid-base extraction procedure. 23 g of the crude product was dissolved in 100 ml 0.5N hydrochloric acid. The turbid yellow solution was filtered to give a clear orange yellow solution which was extracted twice with ethyl acetate (2×10 ml). The aqueous phase was cooled to 0° C. and basified with 6N sodium hydroxide, keeping the temperature of the solution below 15° C. at all times. The yellow solid which precipitated was filtered off and washed thoroughly with water until the washings were neutral to pH paper. The solid was dried overnight in vacuo to give 1.97 g yellow solid, m.p. 249°–50° C. The recovery was about 88%.

Further purification was achieved by recrystallization as described below. The partially purified product from above was dissolved in N,N-dimethylformamide (about 17 ml/g) at 100° C. with vigorous stirring. The solution was filtered hot and set aside to cool overnight. The bright yellow crystals were collected by filtration, m.p. 252°–3° C. Recovery was from 65–77%. Using various analytical procedures, the bright yellow solid was determined to be 5-bromo-6-(2-imidazolin-2-ylamino)quinoxaline.

5-Bromo-6-(2-imidazolin-2-ylamino)-1,2,3,4-tetrahydroquinoxaline

A thick-walled Parr hydrogenation flask was charged with 5-Bromo-6-(2-imidazolin-2-ylamino)quinoxaline (950 mg, 3.23 mmol), platinum oxide (95 mg) and 20 ml of methanol. The contents of the flask were contacted with hydrogen at 15 psi for 15 minutes. The resulting solution was filtered through acid washed silicon dioxide, followed by evaporation of solvent. The resulting tan solid was chromatographed (SiO$_2$; 80/20 CHCl$_3$/CH$_3$OH saturated with NH$_3$ (g)) to yield 820 mg (a yield of 86%) of an off white solid, mp 218°–220° C. Using various Analytical procedures, this off white solid was determined to be 5-bromo-6-(2-imidazolin-2-ylamino)-1,2,3,4-tetrahydroquinoxaline.

EXAMPLE 2

Preparation of
(±)2-Methyl-5-bromo-6-(2-imidazolin-2-ylamino)-1,2,3,4-tetrahydroquinoxaline 2-Methyl-6-nitroquinoxaline A solution of pyruvic aldehyde (Aldrich, 40% solution in H$_2$O, 11.8 g, 65.3 mmol) was added dropwise to a solution of 4-nitro-1,2-phenylenediamine (Aldrich, 10 g, 65.3 mmol) in 150 ml of H$_2$O. The reaction mixture was heated to 80° C. for four hours. The reaction was cooled to room temperature, diluted with H$_2$O and extracted with CHCl$_3$. The organic extracts were dried over MgSO$_4$ and evaporated to yield 10.7 g (a yield of 87%) of a brick red solid. Using various analytical procedures, this solid was determined to be 2-methyl-6 nitroquinoxaline.

2-Methyl-6-Aminoquinoxaline

A thick-walled Parr hydrogenation flask was charged with 2-methyl-6-nitroquinoxaline (10.0 g, 52.9) and CH$_3$OH (200 ml). The flask was flushed with a stream of N$_2$ and 10% by weight palladium on charcoal (500 mg) was added. The flask was pressurized with H$_2$ to 50 psi and maintained at this pressure for three hours. The reaction mixture was filtered through acid washed silicon dioxide and concentrated in vacuo to yield a tan solid. The crude material was chromatographed (SiO$_2$; 95/5 CHCl$_3$/CH$_3$OH saturated with NH$_3$ (g)) and re-crystallized from benzene to yield 7.4 g (a yield of 88%) of a tan solid. Using various analytical procedures, this tan solid was determined to be 2-methyl-6-aminoquinoxaline.

2-Methyl-5-bromo-6-(2-imidazolin-2-ylamino)quinoxaline

By a series of reaction steps analogous to the reaction steps described above in Example 1, the title compound (mp. 260° C.) was prepared starting with 2-methyl-6-aminoquinoxaline in place of 6-aminoquinoxaline.

(+)2-methyl-5-Bromo-6-(2-imidazolin-2-ylamino-1,2,3,4-tetrahydroquinoxaline

A solution of 2-methyl-5-bromo-6-(2-imidazolin-2-ylamino)quinoxaline (40.5 mg, 0,132 mmol) in acetic acid was cooled to 10° C. and carefully treated with NaBH$_4$ (5.0 mg, 0.132 mmol). The reaction mixture was stirred for 15 minutes before the solvent was removed in vacuo. The residue was dissolved in H$_2$O, treated with solid NaOH to pH 13 and extracted with CHCl$_3$. The combined organic extracts were dried over MgSO$_4$ and concentrated in vacuo to yield a yellow oil. The crude material was chromatographed (SiO$_2$, 80/20 CHCl$_3$/CH$_3$OH saturated with NH$_3$ (g)) to yield 21.8 mg (a yield of 53%) of a tan solid, mp 203°–205° C. Using various analytical procedures, this tab solid was determined to be (±) 2-methyl-5-bromo-(2-imidazolin-2-ylamino)-1,2,3,4-tetrahydroquinoxaline.

EXAMPLE 3

Preparation of (±)
3-Methyl-5-bromo-6-(2-imidazolin-2-ylamino)-1,2,3,4-tetrahydroquinoxaline 3-Methyl-6-aminoquinoxaline Pyruvic aldehyde (Aldrich, 892 mg, 4.95 mmol, 40% solution H$_2$O) was added dropwise to a stirred solution of 1,2,4-triaminobenzene hydrochloride (1.0 g, 4.95 mmol) dissolved in 10% aqueous Na$_2$CO$_3$ (15 ml). The mixture was heated at 100° C. for two hours before cooling to room temperature. The mixture was extracted with CHCl$_3$. The combined organic extracts were dried over MgSO$_4$ and concentrated in vacuo to yield a brown solid. The crude product was chromatographed (SiO$_2$, 95/5 CHCl$_3$/CH$_3$OH saturated with NH$_3$ (g)) to yield 616 mg (a yield of 75%) of a yellow crystalline solid. An analytical sample was prepared by recrystallization from benzene, mp 170°–173° C. Using various analytical procedures, the solid was determined to be 3-methyl-6-aminoquinoxaline.

(±)3-Methyl-5-bromo-6-(2-imidazolin-2-ylamino)-1,2,3,4-tetrahydroquinoxaline

By a series of reaction steps analogous to the reaction steps described above in Example 2, the title compound (mp 250°–251° C.) was prepared starting with 3-methyl-6-aminoquinoxaline in place of 2-methyl-6-aminoquinoxaline.

EXAMPLE 4

Preparation of 5-Bromo-6-(2-imidazolin-2-ylamino)-1,4-dimethyl-1,2,3,4-tetrahydroquinoxaline, 5-Bromo-6-(2-imidazolin-2-ylamino)-1-methyl-1,2,3,4-tetrahydroquinoxaline and 5-Bromo-6-(2-imidazolin-2-ylamino)-4-methyl-1,2,3,4-tetrahydroquinxoaline 5-Bromo-6-(2-imidazolin-2-ylamino)quinoxaline (291 mg, 1 mmol) is suspended in CH$_3$OH (2 ml) and treated with glacial acetic acid (1 ml). The reaction mixture is treated with NaCNBH$_3$ (252 mg, 4 mmol) and para-formaldehyde (450 mg, 5 mmol) and stirred at room temperature for 4–8 hours. The reaction mixture is quenched with H₂O (5 ml), basified with solid NaOH (3 g) to pH>12 and extracted with CHCl₃. The CHCl₃ extracts are dried over MgSO₄, concentrated invacuo and chromatographed (SiO₂, 80/20CHCl₃/CH₃OH saturated with NH₃ (g)) to yield the individual title compounds. Each of these title compounds is tested and is found to have one or more useful therapeutic effects which known alpha 2 agonists exhibit.

EXAMPLE 5

Preparation of 5-Bromo-6-(2-imidazolin-2-ylamino)-1,4-diethyl-1,2,3,4-tetrahydroquinoxaline, 5-Bromo-6-(2-imidazolin-2-ylamino)-1-ethyl-1,2,3,4-tetrahydroquinoxaline and 5-Bromo-6-(2-imidazolin-2-ylamino)-4-ethyl-1,2,3,4-tetrahydroquinoxaline The individual title compounds are prepared using the method illustrated in Example 5 except that acetaldehyde (220 mg, 5 mmol) is substituted for paraformaldehyde and the reaction time is 6–12 hours instead of 4–8 hours. Each of these title compounds is tested and is found to have one or more useful therapeutic effects which known alpha 2 agonists exhibit.

EXAMPLE 6

Preparation of 1,2-dihydro-2,2-dimethyl-6-nitro-3-(4H)-quinoxalinone and 3,4-dihydro-3,3-dimethyl-6-nitro-2-(1H)-quinoxalinone To a stirred solution of 4-nitro-1,2-phenylenediamine (Aldrich, 5.0 g, 32.6 mmol) and triethylamine (5.05 g, 50 mmol) in CH₂Cl₂ (50 ml) is added 2-bromo-2-methyl propionyl bromide (Aldrich 7.49 g, 32.6 mmol) dropwise. The mixture is stirred at room temperature until the starting material (4-nitro-1,2-phenylenediamine) is consumed. The reaction is quenched with aqueous NH₄Cl and the organic material is extracted with CH₂Cl₂. The organic extract is washed with H₂O (20 ml), dried over MgSO₄ and concentrated in vacuo. The residue is chromatographed on silica gel with hexanes: ethyl acetate elution to yield a mixture of bromo amide isomers. This mixture is dissolved in CH₂Cl₂ (30 ml) and treated with AgBF₄ (Aldrich, 6.36 g, 32.6 mmol) at room temperature to effect cyclization. After the starting bromo amide isomers are consumed, the reaction is quenched with aqueous NH₄Cl and the organic material is extracted with CH₂Cl₂. The organic extract is washed with H₂O (10 ml), dried over MgSO₄ and concentrated in vacuo. The residue is chromatographed on silica gel with hexanes: ethyl acetate elution to yield the title compounds in pure form. This chromatographing separates the title compounds and allows recovery of each of them individually.

EXAMPLE 7

Synthesis of 6-amino-1,2-dihydro-2,2-dimethyl-6-(2-imidazolin-2-ylamino)-3-(4H)-quinoxalinone A solution of 1,2-dihydro-2,2-dimethyl-6-nitro-3-(4H)-quinoxalinone (663 mg, 3 mmol) in CH₃OH (10 ml) is hydrogenated with 50 psi H₂ (g) at room temperature in the presence of a catalyst of 10% by weight palladium on charcoal (50 mg). After the starting material is consumed, the solution is filtered and concentrated in vacuo to yield 6-amino-1,2-dihydro-2,2-dimethyl-3-(4H)-quinoxalinone.

EXAMPLE 8

Synthesis of 6-amino-5-bromo-1,2-dihydro-2,2-dimethyl-3-(4H)-quinoxalinone hydrobromide A solution of 6-amino-1,2-dihydro-2,2-dimethyl-3-(4H)-quinoxalinone (250 mg, 1.31 mmol) in glacial acetic acid (4 ml) is cooled using a water bath. Bromine (210 mg, 1.31 mmol) in acetic acid (0.25 ml) is added dropwise over a 5 minute period. The mixture is stirred at room temperature for 4 hours and the resulting precipitate is collected by vacuum filtration. The title compound is obtained in pure form after drying in vacuo.

EXAMPLE 9

Synthesis of 2-imidazoline-2-sulfonic acid

2-Imidazolidinethione (66.3 g, 650 mmol), Na₂MoO₄ (5 g, 227 mmol) and NaCl (15 g. 256 mmol) were added to 300 ml H₂O. Although some dissolution occurred, a solid residue remained in the liquid of the mixture. The mixture was cooled to −10° C. using an immersion cooler. 500 ml of a 30% (w/v) aqueous H₂O₂ solution was placed in a jacketed controlled drip rate addition funnel and cooled to 0° C. using an ice/H₂O bath. The aqueous H₂O₂ solution was added to the mixture at a rate of 60 drops/minute. The mixture was stirred for 16 hours at −10° C. During this time, the mixture changed from a white suspension to a dark blue solution to a light blue suspension. At the end of 16 hours, a solid was filtered from the suspension and dried in vacuo. No further purification was needed. 57.8 g (a yield of 52.3%) of the title compound as a white solid, which was characterized spectroscopically, was recovered. This solid was stable when stored in the dark at 0° C. for at least 6 months.

EXAMPLE 10

Synthesis of 5-bromo-1,2-dihydro-2,2-dimethyl-6-(2-imidazolin-2-ylamino)-3-(4H)-quinoxaline A mixture of 6-amino-5-bromo-1,2-dihydro-2,2-dimethyl-3-(4H)-quinoxalinone hydrobromide (479 mg, 1 mmol) and 2-imidazoline-2-sulfonic acid (224 mg, 1.5 mmol) in isobutanol (5 ml) is heated at reflux until the starting hydrobromide material is consumed. The solvent is removed in vacuo and the residue chromatographed on silica gel with CHCl₃: CH₃OH saturated with NH₃ (g) elution to yield the title compound.

EXAMPLE 11

Preparation of 5-bromo-2,2-dimethyl-6-(2-imidazolin-2-ylamino)-1,2,3,4-tetrahydroquinoxaline A suspension of 5-bromo-1,2-dihydro-2,2-dimethyl-6-(2-imidazolin-2-ylamino)-3-(4H)-quinoxalinone (150 mg, 0.45 mmol) and LiALH₄ (17 mg, 0.45 mmol) in tetrahydrofuran (3 ml) is heated and maintained at a temperature of 50°–80° C. until the starting material is consumed. The mixture is cooled to 0° C., 2–3 drops of H₂O is added and the mixture is filtered. The solution is concentrated in vacuo to yield a residue which is chromatographed on silica gel with CHCl₃: CH₃OH saturated with NH₃ (g) elution to produce the title compound.

EXAMPLE 12

Preparation of 5-bromo-3,4-dihydro-3,3-dimethyl-6-(2-imidazolin-2-ylamino)-2-(1H)-quinoxalinone By a series of reaction steps analogous to the steps described above in Examples 7 to 10, the title compound is prepared starting with 3,4-dihydro-3,3-dimethyl-6-nitro-2-(1H)-quinoxalinone in place of 1,2 dihydro-2,2-dimethyl-6-nitro-3-(4H)-quinoxalinone.

EXAMPLE 13

Preparation of 5-bromo-3,4-dihydro-3,3-dimethyl-6-(2-imidazolin-2-ylamino)-1,2,3,4-tetrahydro-quinoxaline Using the procedure illustrated in Example 11, the title compound is prepared starting with 5-bromo-3,4-dihydro-3,3-dimethyl-6-(2-imidazolin-2-ylamino)-2-(1H)-quinoxaline in place of 5-bromo-1,2-dihydro-2,2-dimethyl-6-(2-imidazolin-2-ylamino)-3-(4H)-quinoxalinone.

EXAMPLES 14 TO 17

The quinoxaline derivatives produced in Examples 10 to 13 are tested for activity using the following in vitro methods.

Rabbit Vas Deferens: Alpha 2 Adrenergic Receptors

New Zealand white rabbits (2–3 kg) are killed by $CO_2$ inhalation and the vasa deferentia is removed. The prostatic ends of the vasa deferentia (2–3 cm lengths) are mounted between platinum ring electrodes in 9 ml organ baths and bathed in Krebs bicarbonate solution of the following composition (millimolar): NaCl 118.0; KCl 4.7; $CaCl_2$ 2.5; $MgSO_4$ 1.2; $KH_2PO_4$ 1.2; glucose 11.0; $NaHCO_3$ 25.0; which solution is maintained at 35° C. and bubbled with 95% $O_2$ and 5% $CO_2$. The initial tension of the vas deferens is 0.5 g. The tissues are left to equilibrate for 30 minutes before stimulation is started. Vasa are then field stimulated (0.1 Hz, 2 ms pulse width at 90 mA) using a square wave stimulator (WPI A310 Accupulser with A385 stimulus). The contractions of the tissue are recorded isometrically using Grass FT03 force-displacement transducers and displayed on a Grass Model 7D polygraph. A cumulative concentration-response relationship is obtained for the quinoxaline derivative being tested with a 4 minute contact time at each concentration. Each of the quinoxaline derivatives of Examples 10 to 13 is effective to reduce the response height. Therefore, such compounds may be properly classified as Alpha 2 agonists since they are also inhibited pharmacologically by treatment with rauwolscine.

EXAMPLES 18 TO 21

Each of the quinoxaline derivatives produced in Examples 10 to 13 is tested for renal and blood pressure effects using the following method.

Young male (20–24 weeks old) Sprague-Dawley rats are used. Under ketamine (60 mg/kg b.wt. i.m.) and pentobarbital (i.p. to effect) anesthesia, medical grade plastic tubes are implanted into the abdominal aorta and vena cava via the femoral vessels. In addition, a Silastic-covered stainless steel cannula is sewn in the urinary bladder. After the surgery, the rats are housed individually and are allowed free access to food and water until the day of the experiment.

For about 7 to 10 days before surgery and during recovery, the rats are accustomed to a restraining cage by placement in the cage for 2 to 3 hours every 2nd and 3rd day. The cage is designed for renal clearance studies (a model G Restrainer sold by Braintree Scientific, Inc., Braintree, Mass.). The animals' adjustment to the cage is judged by the stability of blood pressure and heart rate.

For an experiment, a rat is placed in the restraining cage, and the arterial line is connected to a Statham pressure transducer and a Beckman Dynograph R61 to monitor the mean arterial blood pressure, hereinafter referred to as MAP. The venous line is connected to an infusion pump system for infusion of replacement fluid. The quinoxaline derivative is administered intraduodenally by cannula. The bladder cannula was extended with a silastic tube to facilitate collection of urine in preweighed tubes. The volume of urine is measured gravimetrically. Body weight is recorded before and after the experiment.

Throughout the experiments, 0.9% NaCl containing 10% polyfructosan (Inutest) and 1% sodium PAH is infused at a rate of 20 microliters/min. An equilibration period of 60 minutes is followed by two consecutive 30 minute control clearance periods. Then, the quinoxaline derivative is administered for 90 minutes. Urine collection is resumed 10 minutes after the start of quinoxaline derivative administration. By this time the washout of the bladder cannula dead space (approximately 200 microliters) is completed. Three additional clearance measurements are made. Blood samples (150 microliters) are collected at the midpoint of urine collections. Plasma is separated and saved for analyses, and the cells are resuspended in saline and returned to the animals. Water and sodium loss is carefully replaced i.v. by a variable speed infusion pump.

Results of these tests indicate that the present quinoxaline derivatives produce renal effects, e.g., increased renal fluid flow. The effect on blood pressure of such derivatives is limited relative to such renal effects.

EXAMPLES 22 TO 25

Each of the quinoxaline derivative produced in Examples 10 to 13 is tested for anti-diarrheal effects and blood pressure effects using the following method.

Cecectomies are performed in unfasted rats in a conventional manner. The cecectomized rats are put into individual wire-bottomed cages placed over sheets of clean paper, and deprived of food and water for the duration of the assay. The MAP is monitored, as described in Examples 17 to 20, throughout the assay. Rats are given a 2 hour acclimatization period prior to the start of the assay in order to eliminate sporadic episodes of anxiety-induced defecation. During this period they are observed also for consistent occurrences of pelleted feces; an animal producing other than a pelleted stool is disqualified from the study.

Diarrhea is induced with oral administration of 16,16-dimethyl prostaglandin $E_2$ (dmPGE$_2$) in 3.5% EtOH. The quinoxaline derivative is administered by gavage after the onset of diarrheal episodes. The cage papers are removed and examined at 30 minute intervals for dmPGE$_2$-induced diarrhea. Fecal output is recorded at each interval and fecal consistency is assigned a numerical score in each experimental group as follows: 1=normal pelleted stool; 2=soft-formed stools; 3=water stool and/or diarrhea. The fecal output index (FOI) is defined as the summation of the number of defecation episodes and their ranked consistency score within an observation period.

Results of these tests indicate that the quinoxaline derivatives produced in Examples 10 to 13 provide substantial anti-diarrheal effects. Further, such anti-diarrheal effects are produced with no or relatively limited effects on blood pressure.

While this invention has been described with respect to various specific examples and embodiments, it is to be understood that the invention is not limited thereto and that it can be variously practiced within the scope of the following claims.

What is claimed is:

1. A method of treating a mammal comprising administering to a mammal an effective amount to provide a desired therapeutic effect in said mammal of a compound selected from the group consisting of those have the formula

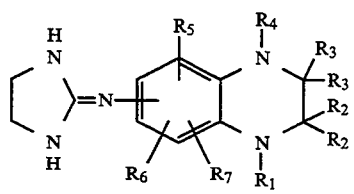

, pharmaceutically acceptable acid addition salts thereof and mixtures thereof, wherein $R_1$ and $R_4$ are independently selected from the group consisting of H and alkyl radicals having 1 to 4 carbon atoms; the $R_2$s are independently selected from H or alkyl radicals having 1 to 4 carbon atoms or are, together, oxo; the $R_3$s are independently selected from H or alkyl radicals having 1 to 4 carbon atoms or are, together, oxo; the 2-imidazolin-2-ylamino group may be in any of the 5-, 6-, 7- or 8-positions of the quinoxaline nucleus; and $R_5$, $R_6$ and $R_7$ each is located in one of the remaining 5-, 6-, 7- or 8-positions of the quinoxaline nucleus and is independently selected from the group consisting of Cl, Br, H and alkyl radicals having 1 to 3 carbon atoms, said desired therapeutic effect being selected from the group comprising reduction in peripheral pain, and reduction in or prevention of at least one effect of ischemia.

2. The method of claim 1 wherein said desired therapeutic effect is a reduction in peripheral pain.

3. The method of claim 1 wherein said desired therapeutic effect is reduction in or prevention of at least one effect of ischemia.

4. The method of claim 1 at least one of the $R_2$s and at least one of the $R_3$s is H.

5. The method of claim 1 wherein the 2-imidazolin-2-ylamino group is in the 6-position of the quinoxaline nucleus, $R_5$ is in the 5-position of the quinoxaline nucleus and is selected from the group consisting of Cl, Br and alkyl radicals containing 1 to 3 atoms, and $R_6$ and $R_7$ are both H.

6. The method of claim 1 wherein each of $R_1$ and $R_4$ is H.

7. The method of claim 1 wherein each of the $R_2$s and each of the $R_3$s is independently selected from the group consisting of H and alkyl radicals having 1 to 4 carbon atoms.

8. The method of claim 1 wherein at least one of the $R_2$s is different from at least one of the $R_3$s.

9. The method of claim 7 wherein at least one of the $R_2$s is different from at least one of the $R_3$s.

10. The method of claim 4 wherein one of the $R_2$s and one of the $R_3$s are independently selected from the group consisting of H and methyl radical.

11. The method of claim 10 wherein at least one of the $R_2$s is different from at least one of the $R_3$s.

12. The method of claim 1 wherein $R_5$ is Br.

13. The method of claim 1 wherein said formula is:

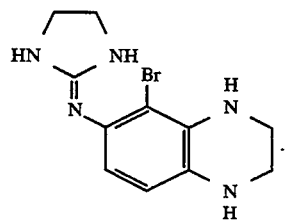

14. The method of claim 1 wherein said formula is:

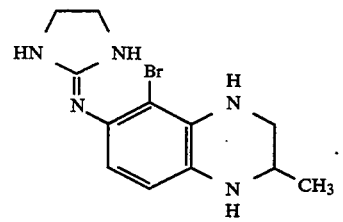

15. The method of claim 1 wherein said formula is:

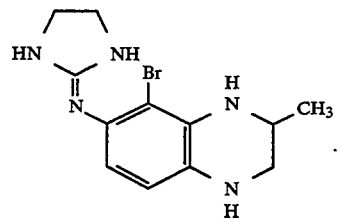

16. The method of claim 1 wherein said formula is:

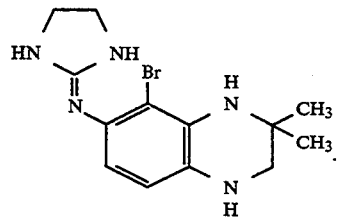

17. The method of claim 1 wherein said formula is:

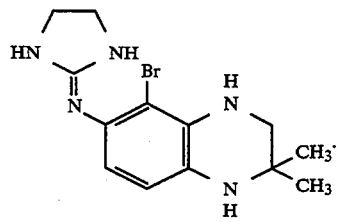

18. The method of claim 1 wherein said formula is:

19
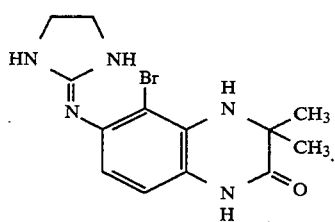
19. The method of claim 1 wherein said formula is:
20
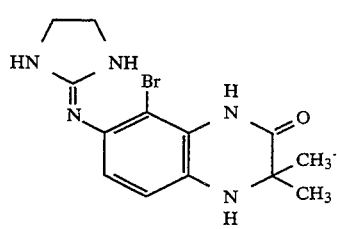
* * * * *

UNITED STATES PATENT AND TRADEMARK OFFICE
CERTIFICATE OF CORRECTION

PATENT NO. : 5,418,234
DATED : May 23, 1995
INVENTOR(S) : Gluchowski et al

It is certified that error appears in the above-indentified patent and that said Letters Patent is hereby corrected as shown below:

Column 3, line 33, delete "thereof"--.

Column 3, line 33; after "such as" insert --,--.

Column 4, line 67; delete "ethylenediamine" and insert in place thereof --ethylene diamine--.

Column 7, line 21; delete "0.15" and insert in place thereof --0.5--.

Column 10, line 68; delete "242/144 C" and insert in place thereof --242-4°C--.

Column 12, line 13; delete "0,132" and insert in place thereof --0.132--.

Signed and Sealed this

Twenty-fourth Day of September, 1996

Attest:

BRUCE LEHMAN

*Attesting Officer*　　*Commissioner of Patents and Trademarks*